United States Patent [19]

Inoue et al.

[11] Patent Number: 5,214,193
[45] Date of Patent: May 25, 1993

[54] PRODUCTION OF BISPHENOL MONOESTER

[75] Inventors: Kikumitsu Inoue; Manji Sasaki, both of Nishinomiya; Kazuaki Yamamoto, Ibaraki; Shinichi Yachigo, Toyonaka, all of Japan

[73] Assignee: Sumitomo Chemical Company, Limited, Osaka, Japan

[21] Appl. No.: 834,373

[22] Filed: Feb. 12, 1992

[30] Foreign Application Priority Data

Feb. 18, 1991 [JP] Japan .................. 3-023539
Apr. 25, 1991 [JP] Japan .................. 3-095377

[51] Int. Cl.$^5$ .................. C07C 67/03; C07C 67/08; C07C 67/14
[52] U.S. Cl. .................. 560/140; 560/144; 562/493
[58] Field of Search .................. 560/140; 562/493

[56] References Cited

U.S. PATENT DOCUMENTS

| | | | |
|---|---|---|---|
| 3,984,372 | 10/1976 | Cottman | 524/99 |
| 4,365,032 | 12/1982 | Yosizato et al. | 560/140 X |
| 4,562,281 | 12/1985 | Takahashi et al. | 560/140 X |
| 4,774,274 | 9/1988 | Takata et al. | 560/140 X |

FOREIGN PATENT DOCUMENTS 0322166 6/1989 .

Primary Examiner—José G. Dees
Assistant Examiner—Vera C. Clarke
Attorney, Agent, or Firm—Stevens, Davis, Miller & Mosher

[57] ABSTRACT

A bisphenol monoester represented by the formula (I):

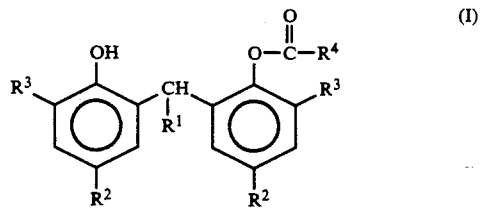

wherein $R^1$ is hydrogen or alkyl, $R^2$ and $R^3$ are each alkyl, and $R^4$ is alkyl, alkenyl or phenyl, is produced by continuous two step reactions in which an aldehyde $R^1$-CHO and 2,4-dialkylphenol are subjected to a condensation reaction in a $C_6$-$C_{10}$ aliphatic or $C_6$-$C_{12}$ aromatic hydrocarbon solvent, and then a resulting bisphenol compound dissolved in the solvent is subjected to an esterification with a carboxylic acid $R^4$—COOH or its derivative. Prior to the esterification, the organic layer containing the bisphenol compound is subjected to a dehydration treatment, thereby enabling the two steps to proceed continuously without isolating the intermediate bisphenol compound. A purification process for the bisphenol monoester of the formula (I) is also disclosed in which the monoester is purified from a mixed solvent comprising a $C_6$-$C_{12}$ aromatic hydrocarbon solvent and a $C_1$-$C_8$ alcohol or $C_2$-$C_3$ aliphatic nitrile solvent.

23 Claims, No Drawings

PRODUCTION OF BISPHENOL MONOESTER

BACKGROUND OF THE INVENTION

The present invention relates to a production process and a purification process of a bisphenol monoester represented by the following formula (I):

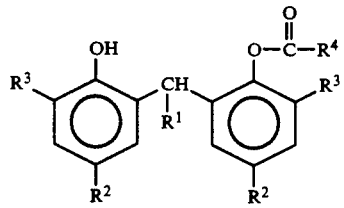
(I)

$R^1$ is hydrogen or an alkyl of 1 to 3 carbon atoms, $R^2$ and $R^3$ independently of one another are each an alkyl of 1 to 5 carbon atoms, and $R^4$ is an alkyl of 1 to 3 carbon atoms, an alkenyl of 2 to 4 carbon atoms or phenyl.

The bisphenol monoester represented by the above formula (I) is useful as heat deterioration inhibitors in production or processing of butadiene polymers such as butadiene rubber (BR), styrene/butadiene copolymer rubber (SBR) and styrene/butadiene block copolymer rubber or resin (SBS) or as stabilizers for various synthetic resins, for example, polyolefins such as polyethylene and polypropylene.

For production of the bisphenol monoester represented by the formula (I), there have been known a process which comprises reacting a bisphenol compound represented by the following formula (IV):

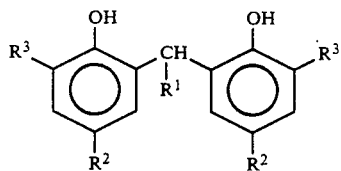
(IV)

wherein $R^1$, $R^2$ and $R^3$ are as defined above, with a carboxylic acid represented by the following formula (VI):

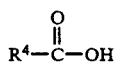
(VI)

wherein $R^4$ is as defined above, using a halogenating agent in the presence of a dehydrohalogenating agent (U.S. Pat. No. 4,562,281 and U.S. Pat. No. 4,774,274), and a process which comprises reacting an acid halide or acid anhydride derived from the carboxylic acid represented by the above formula (VI) with the bisphenol compound represented by the above formula (IV) in the presence of a basic compound such as an amine or a pyridine (U.S. Pat. No. 4,365,032 and U.S. Pat. No. 3,984,372).

The bisphenol compound represented by the above formula (IV) is generally produced by condensation reaction of an aldehyde represented by the following formula (II):

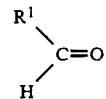
(II)

wherein $R^1$ is as defined above, with a dialkylphenol represented by the following formula (III):

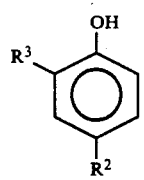
(III)

wherein $R^2$ and $R^3$ are as defined above.

However, since the above-mentioned known processes for producing the bisphenol monoester represented by the formula (I) use the isolated and purified bisphenol compound (IV), loss in dissolution is caused in isolation and purification of the bisphenol oompound, resulting in reduction of yield based on the dialkylphenol (III) and besides, much time is required for filtration and drying. Thus, the processes have not necessarily been satisfactory in production on an industrial scale.

Furthermore, for purification of the bisphenol monoester represented by the formula (I) there have been known a process according to which recrystallization is carried out using petroleum ether or n-hexane as described in Examples 11 and 12 of U.S. Pat. No. 3,984,372, and a process according to which a solvent such as toluene or N,N-dimethylacetamide used for the reaction is partially or completely distilled off and toluene or n-hexane is added to the residue to carry out purification as described in Examples of U.S. Pat. No. 4,365,032, U.S. Pat. No. 4,562,281 and U.S. Pat. No. 4,774,274.

However, these processes are not satisfactory in quality of the desired product because purification effect is low owing to the small difference between the solubility of the desired bisphenol monoester contained in the crude product to be purified and that of impurities. Furthermore, these processes are also not satisfactory in production on an industrial scale since production equipments become complicated when the solvent is to be recovered for economical reasons.

SUMMARY OF THE INVENTION

One of the objects of the present invention is to provide a satisfactory process for producing the bisphenol monoester of the formula (I) in an industrial scale operation.

Another object of the invention is to provide a process for producing the bisphenol monoester of the formula (I) starting from the dialkylphenol of the formula (III) continuously, with high quality, with high yield and with economy.

A further object of the invention is to provide satisfactory process for purifying the bisphenol monoaester of the formula (I) in an industrial scale operation.

A still further object of the invention is to provide a process for purifying the bisphenol monoester of the formula (I) by crystallization, with high quality, with high yield and with economy.

As a result of intensive investigations, it has been found that the desired product (I) having excellent quality can be economically produced, with high yield, continuously from the dialkylphenol (III) without isolating the bisphenol compound (IV), by using a particular solvent and removing water from the condensation reaction mixture prepared by the reaction of the aldehyde (II) and the dialkylphenol (III).

Further, it has also been found that the desired product (I) having excellent quality can be economically obtained with high yield by crystallization using a particular mixed solvent.

The present invention has been accomplished based on the above findings.

Thus, the invention provides a process for producing a bisphenol monoester represented by the above formula (I) comprising the steps of subjecting an aldehyde represented by the above formula (II) to a condensation reaction with a dialkylphenol represented by the above formula (III) in a solvent selected from aliphatic hydrocarbons of 6 to 10 carbon atoms and aromatic hydrocarbons of 6 to 12 carbon atoms to obtain a bisphenol compound represented by the above formula (IV), subjecting an organic layer containing the bisphenol compound to a dehydration treatment, and subjecting the dehydrated organic layer, without isolating the bisphenol compound, to a reaction with a carboxylic compound represented by the formula (V):

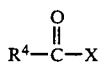

wherein $R^4$ is as defined above, and X is hydroxyl, halogen, an alkoxy of 1 to 3 carbon atoms, or a group of

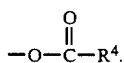

The invention also provides a process for purifying a crude product of the bisphenol monoester represented by the above formula (I) by using a mixed solvent comprising a first solvent selected from aromatic hydrocarbons of 6 to 12 carbon atoms and a second solvent selected from alcohols of 1 to 8 carbon atoms and aliphatic nitriles of 2 to 3 carbon atoms, and crystallizing the desired bisphenol monoester from the mixed solvent.

DESCRIPTION OF THE INVENTION

The alkyl represented by $R^1$ in the aldehyde of the formula (II) used for production of the bisphenol monoester of the formula (I) includes methyl, ethyl, n-propyl and isopropyl. Examples of the aldehyde represented by the formula (II) are formaldehyde, acetaldehyde, propionaldehyde, n-butylaldehyde and isobutylaldehyde.

The alkyl represented by $R^2$ and $R^3$ in the dialkylphenol represented by the formula (III) includes, for example, methyl, ethyl, n-propyl, isopropyl, n-butyl, isobutyl, sec-butyl, tert-butyl, pentyl, tert-pentyl and the like. $R^2$ and $R^3$ may be identical or different. Examples of the dialkylphenol represented by the formula (III) are 2,4-di-t-pentylphenol, 2,4-di-t-butylphenol, 2-t-butyl-4-methylphenol, 2-t-butyl-4-ethylphenol, 2-t-butyl-4-propylphenol, 2-t-butyl-4-isopropylphenol and the like.

Therefore, examples of the bisphenol compound represented by the formula (IV) which is obtained by the condensation reaction are as follows.
2,2'-ethylidenebis(4,6-di-t-pentylphenol),
2,2'-methylenebis(4,6-di-t-pentylphenol),
2,2'-ethylidenebis(4,6-di-t-butylphenol),
2,2'-methylenebis(4,6-di-t-butylphenol),
2,2'-propylidenebis(6-t-butyl-4-methylphenol),
2,2'-ethylidenebis(6-t-butyl-4-methylphenol),
2,2'-methylenebis(6-t-butyl-4-nethylphenol),
2,2'-methylenebis(6-t-butyl-4-ethylphenol),
2,2'-ethylidenebis(6-t-butyl-4-propylphenol),
2,2'-ethylidenebis(6-t-butyl-4-isopropylphenol), and the like.

The carboxylic compound represented by the formula (V) can be a free carboxylic acid, a carboxylic acid halide, a lower alkyl ester of carboxylic acid or a carboxylic acid anhydride. Examples of the carboxylic compound of the formula (V) are carboxylic acids such as acetic acid, propionic acid, butyric acid, acrylic acid, methacrylic acid, crotonic acid, 3-butenoic acid, and benzoic acid, halides of these carboxylic acids such as chlorides, bromides and iodides, lower alkyl esters of these carboxylic acids such as methyl esters, ethyl esters and propyl esters, and anhydrides of these carboxylic acids.

The bisphenol monoester of the formula (I) produced by the present invention is a monoester of the bisphenol compound represented by the formula (IV) with the carboxylic compound represented by the formula (V), and especially, the compounds in which $R^4$ is an alkenyl are preferred as stabilizers for various polymers. Preferable examples of the bisphenol monoesters represented by the formula (I) are enumerated below.
2-[1-(2-hydroxy-3,5-di-t-pentylphenyl)ethyl]-4,6-di-t-pentylphenyl acrylate,
2-[1-(2-hydroxy-3,5-di-t-pentylphenyl)ethyl]-4,6-di-t-pentylphenyl methacrylate,
2-(2-hydroxy-3,5-di-t-pentylbenzyl)-4,6-di-tpentylphenyl acrylate,
2,4-di-t-butyl-6-[1 (3,5-di-t-lutyl-2-hydroxyphenyl)ethyl]phenyl acrylate,
2,4-di-t-butyl-6-(3,5-di-t-butyl-2-hydroxybenzyl)phenyl acrylate,
2,4-di-t-butyl-6-[1-(3,5-di-t-butyl-2-hydroxyphenyl)ethyl]phenyl methacrylate,
2-t-butyl-6-(3-t-butyl-2-hydroxy-5-methylbenzyl)-4-methylphenyl acrylate,
2-t-butyl-6-[1-(3-t-butyl-2-hydroxy-5-methylphenyl)ethyl]-4-methylphenyl acrylate,
2-t-butyl-6-(3-t-butyl-2-hydroxy-5-methylbenzyl)-4-methylphenyl methacrylate,
2-t-butyl-6-[1-(3-t-butyl-2-hydroxy-5-methylphenyl)propyl]-4-methylphenyl acrylate,
2-t-butyl-6-(3-t-butyl-5-ethyl-2-hydroxybenzyl)4-ethylphenyl acrylate,
2-t-butyl-6-[1-(3-t-butyl-2-hydroxy-5-propylphenyl)ethyl]-4-propylphenyl acrylate,
2-t-butyl-6-[1-(3-t-butyl-2-hydroxy-5-isopropylphenyl)ethyl]-4-isopropylphenyl acrylate, and the like.

In the present invention, the condensation reaction between the aldehyde represented by the formula (II) and the dialkylphenol represented by the formula (III) is carried out using an aliphatic hydrocarbon of 6 to 10 carbon atoms or an aromatic hydrocarbon of 6 to 12 carbon atoms as a solvent. The aliphatic hydrocarbon of 6 to 10 carbon atoms includes, for example, n-hexane, n-heptane, n-octane, n-nonane, n-decane, cyclohexane and the like. The aromatic hydrocarbon of 6 to 12 carbon atoms includes, for example, benzene, toluene, ethylbenzene, xylene, cumene, cymene, chlorobenzene and the like. These solvents may be used each alone or in combination of two or more. Among them, aromatic hydrocarbons are preferred and toluene and xylene are especially preferred. Amount of the solvent is preferably about 1–100% by weight based on the amount of the dialkylphenol of the formula (III).

The reaction is carried out preferably in the presence of a catalyst and a surface active agent. As the catalysts, there may be normally used acid catalysts such as sulfuric acid, hydrochloric acid, toluenesulfonic acid and phosphoric acid. As the surface active agents are generally used anionic surface active agents high in hydrophilic-lipophilic balance (HLB).

Temperature for the condensation reaction is preferably in the range of about 60°–110° C., and more preferably about 70°–100° C. This reaction usually proceeds under atmospheric pressure, but may also be carried out in pressurized state. Normally, a reaction time of about 1 to 20 hours suffices and 2 to 10 hours is more preferred.

According to the present invention, without isolating the bisphenol compound of the formula (IV), the reaction mixture obtained by the condensation reaction is used, as it is, for the reaction with the carboxylic oompound represented by the formula (V). However, prior to the reaction with the carboxylic compound, an aqueous layer produced by the condensation reaction is separated and removed, and an organic layer containing the bisphenol compound of the formula (IV) is subjected to a dehydration treatment. Preferably, the solvent used in the reaction is further added to the reaction mixture containing water by-produced in the condensation reaction and then, the reaction mixture is separated into an aqueous layer and an organic layer, which is, if necessary, subjected to aftertreatments such as neutralization and washing with water. Amount of the additional solvent is preferably at least 30% by weight, more preferably 40–200% by weight based on the amount of the dialkylphenol of the formula (III). Use of an excess solvent causes increase in burden of distillation for recovery and is not preferred.

The thus obtained organic layer contains water. In general, esterification reaction per se of the bisphenol compound of the formula (IV) hates water. Therefore, water content in the bisphenol compound of the formula (IV) which is a starting material must be as low as possible. Accordingly, in the present invention, the organic layer containing the bisphenol compound of the formula (IV) is subjected to a dehydration treatment before the reaction with the carboxylic compound of the formula (V).

Removal of water contained in the organic layer can be carried out, for example, by heating or by using a dehydrating agent.

When the dehydration is effected by heating, generally, the organic layer containing the bisphenol compound of the formula (IV) is heated and solvent and water in the form of vapor are led into a suitable condenser, where water is distilled out of the system utilizing the difference in boiling point and the condensed solvent is refluxed to the organic layer, or the organic layer is heated under such conditions that evaporation of the solvent is as little as possible to expel the vapor mainly composed of water from the system. This dehydration by heating is preferably carried out under reduced pressure, but may also be carried out under normal pressure.

When the dehydration is carried out using a dehydrating agent, phosphorus oxychloride, phosphorus oxybromide, o- or p-toluenesulfonyl chloride, a carboxylic acid anhydride or the like is used as the dehydrating agent. However, by-products may be formed depending on the dehydrating agent used, and hence, dehydration by heating is preferred and dehydration by refluxing is especially preferred.

In the present invention, water content in the organic layer is reduced to preferably 0.1% by weight or less, more preferably 0.05% by weight or less. If the water content in the organic layer is more than 0.1% by weight, reduction of yield or production of by-products is apt to occur in the subsequent esterification reaction and this is not preferred.

As mentioned above, by subjecting the organic layer containing the bisphenol compound of the formula (IV) to the dehydration treatment, the condensation reaction mixture can be used, as it is, for the reaction with the carboxylic compound represented by the formula (V) without isolating the bisphenol compound (IV) which is a starting material for the bisphenol monoester of the formula (I).

The bisphenol monoester of the formula (I) is obtained by reacting the above-obtained reaction mixture containing the bisphenol compound of the formula (IV) with the carboxylic compound of the formula (V). In this reaction, it is preferred to use the carboxylic compound (V) in a molar ratio of about 0.7–1.7 times, especially about 1–1.5 times, the mole of the bisphenol compound (IV).

The reaction per se between the bisphenol compound (IV) and the carboxylic compound (V) can be carried out by various known processes. For example, when the carboxylic compound (V) is an acid halide or an acid anhydride, the reaction is carried out in the presence of a basic compound such as an amine or a pyridine. When the carboxylic compound (V) is a lower alkyl ester, the bisphenol monoester of the formula (I) is produced by an ester exchange reaction.

It is especially preferred in the present invention to react the compound of the formula (V) where X is hydroxyl, namely, the carboxylic acid of the formula (VI) with the reaction mixture containing the bisphenol compound (IV). In this case, the reaction is carried out using a dehydrohalogenating agent and a halogenating agent.

The dehydrohalogenating agents used here include, for example, tertiary amines such as triethylamine, dimethylaniline, N,N-dimethylbenzylamine and tetramethylurea, and pyridine compounds such as pyridine and 4-(N,N-dimethylamino)pyridine. Among them, especially preferred is triethylamine which is inexpensive and can be recovered with ease.

As the halogenating agents, there may be used, for example, phosphorus oxychloride, phosphorus oxybromide, o-toluenesulfonyl chloride and p-toluenesulfonyl chloride. Phosphorus oxychloride is especially preferred.

In the reaction between the reaction mixture containing the bisphenol compound of the formula (IV) and the carboxylic acid of the formula (VI), amount of the halogenating agent in terms of halogen atom in the halogenating agent is preferably about 0.7–3 times, more preferably about 0.8–2.5 times, the mole of the carboxylic acid (VI). More preferred amount varies depending on the kind of the halogenating agent used. For example, when the halogenating agent is phosphorus oxychloride or phosphorus oxybromide, it is used in a molar ratio of preferably about 0.4–1 time, more preferably about 0.5–0.8 time, the mole of the carboxylic acid (VI). When the halogenating agent is o- or p-toluenesulfonyl chloride, it is used in a molar ratio of preferably about 0.7–1.6 times, more preferably about 0.8–1.2 times, the mole of the carboxylic acid (VI).

The dehydrohalogenating agent is used in an amount of preferably about 0.8–1.2 moles based on 1 mole of halogen atom in the halogenating agent. More preferred amount of the dehydrohalogenating agent varies depending on the kind of the halogenating agent. For example, when the halogenating agent is phosphorus oxychloride or phosphorus oxybromide, the dehydrohalogenating agent is used in a molar ratio of preferably about 2.7–3.8 times, more preferably about 2.9–3.5 times, the mole of the halogenating agent. When the halogenating agent is o- or p-toluenesulfonyl chloride, the dehydrohalogenating agent is used in a molar ratio of preferably about 0.8–2.6 times, more preferably 0.9–2.4 times, the mole of the halogenating agent.

Sequence of addition of the carboxylic acid (VI), the dehydrohalogenating agent and the halogenating agent to the reaction mixture containing the bisphenol compound (IV) is not critical. For example, three of the carboxylic acid (VI), the dehydrohalogenating agent and the halogenating agent can be added in combination to the reaction mixture containing the bisphenol compound (IV). Moreover, the carboxylic acid (VI) can be added to the reaction mixture containing the bisphenol compound (IV) and then, the dehydrohalogenating agent and the halogenating agent can be added in combination thereto. Alternatively, the carboxylic acid (VI) and the dehydrohalogenating agent are added to the reaction mixture containing the bisphenol compound (IV) and then, the halogenating agent can be added thereto. However, considering the yield, it is preferred to react the bisphenol compound (IV) with the carboxylic acid (VI) using the halogenating agent in the presence of the dehydrohalogenating agent. That is to say, it is preferred to add the carboxylic acid (VI) and the dehydrohalogenating agent to the reaction mixture containing the bisphenol compound (IV) and then add the halogenating agent thereto.

Temperature for the esterification reaction between the bisphenol compound (IV) and the carboxylic compound (V) is preferably about 0°–120° C., more preferably about 20°–100° C. This reaction proceeds under atmospheric pressure, but may also be carried out under pressurized state. Generally, a reaction time of about 0.5–20 hours suffices and more preferred is about 1–10 hours.

After completion of the reaction, the acid salt of dehydrohalogenating agent which is by-produced when, for example, a free carboxylic acid or an acid halide is used as the carboxylic compound (V) is removed by filtration or by dissolving with addition of water to the reaction mixture and, if necessary, the reaction mixture is subjected to after-treatments such as neutralization and washing with water. The thus obtained reaction mixture is crystallized by cooling as it is or after a suitable amount of solvent is recovered by distillation, whereby the desired product can be obtained. As a solvent in the crystallization, one which is used for the reaction can be used as it is or other solvent can also be used. As the crystallization solvent which is different from the reaction solvent, there may be used alcohols such as methanol and ethanol and ketones such as acetone and ethyl methyl ketone. The resulting desired product can further be purified by recrystallization and the like.

The bisphenol monoester of the formula (I) is preferably purified, as described above, by using a mixed crystallization solvent comprising a first solvent of an aromatic hydrocarbon and a second solvent of an alcohol or an aliphatic nitrile, and crystallizing the bisphenol monoester from the mixed solvent. The bisphenol monoesters to be purified may be those produced by the above-mentioned process, but are not limited to them. Thus, the crude bisphenol monoester produced by any other process and represented by the above formula (I) can be purified by the purification process of the present invention.

As mentioned above, the bisphenol monoester represented by the formula (I) which is to be purified in the present invention can usually be produced by the reaction of a 2,2'-alkylidenebis(4,6-dialkylphenol) with a carboxylic acid or a derivative thereof. The starting 2,2'-alkylidenebis(4,6-dialkylphenol) can be produced by condensing the corresponding 2,4-dialkylphenol with an aldehyde.

The alkyl represented by $R^1$ in the formula (I) includes methyl, ethyl, n-propyl and isopropyl, $R^1$ is preferably hydrogen or methyl. The alkyls represented by $R^2$ and $R^3$ include, for example, methyl, ethyl, n-propyl, isopropyl, n-butyl, isobutyl, sec-butyl, tert-butyl, n-pentyl, tert-pentyl and the like. Especially, $R^3$ is preferably an alkyl having a quaternary carbon, namely, tert-butyl or tert-pentyl. The alkyl represented by $R^4$ includes methyl, ethyl, n-propyl and isopropyl. The alkenyl represented by $R^4$ includes, for example, vinyl, isopropenyl, 1-propenyl, 1-butenyl and the like. $R^4$ may also be phenyl.

Among the bisphenol monoesters represented by the formula (I), those which have an alkenyl as $R^4$ are preferably used as stabilizers for various polymers. Preferred examples of these bisphenol monoesters are as mentioned above.

In the present invention, such bisphenol monoester is purified by crystallization. In this case, as a crystallizing solvent is used a mixed solvent comprising a first solvent selected from aromatic hydrocarbons of 6 to 12 carbon atoms and a second solvent selected from alcohols of 1 to 8 carbon atoms and aliphatic nitriles of 2 to 3 carbon atoms.

The aromatic hydrocarbons of 6 to 12 carbon atoms as the first solvent include, for example, benzene, toluene, xylene, ethylbenzene, cumene, cymene, chlorobenzene and the like. These may be used each alone or in combination of two or more as the first solvent of the mixed solvent, but normally, either one of them is used. Among these aromatic hydrocarbons, toluene and xylene are preferred and xylene is especially preferred.

The alcohols of 1 to 8 carbon atoms as one of the second solvent include, for example, methanol, ethanol, n-propanol, isopropanol, n-butanol, isobutanol, tert-butanol, n-pentanol, n-octanol, 2-ethylhexanol, cyclohexanol and the like. The aliphatic nitriles of 2 to 3 carbon atoms include acetonitrile and propiononitrile. These alcohols and aliphatic nitriles can be used each alone or in combination of two or more as the second solvent of the mixed solvent. Among these second solvents, alcohols are preferred and, methanol is especially preferred because it is inexpensive and can be easily recovered.

Generally, the aromatic hydrocarbons used as the first solvent in the mixed solvent are also used as the reaction solvent in production of the bisphenol monoester and act as a dissolving agent in crystallization since solubility of the bisphenol monoester is high. Therefore, when the aromatic hydrocarbon is used as the reaction solvent, the reaction step can be shifted to the recrystallizing step while the reaction mixture is in the form of solution in which the aromatic hydrocarbon remains. The alcohols or aliphatic nitriles which are the second solvent are used for controlling the solubility of the bisphenol monoester in the first solvent thereby to improve the yield and the purification effect or for inhibition of scale deposition on crystallizing apparatuses. When the first solvent or the second solvent is used singly, quality or yield of the desired product is deteriorated. Especially when the second solvent is used alone, the aromatic hydrocarbon solvent used for monoesterification reaction must be distilled out of the system and this is not preferred also for economical reasons in production on an industrial scale.

As explained above, especially when the aromatic hydrocarbon is used as a reaction solvent in the monoesterification, the bisphenol monoester to be crystallized in the present invention may be in the form of solution of the reaction mixture containing said aromatic hydrocarbon or may be, of course, a crystallized product obtained by removing the solvent from the reaction mixture. Especially, in the production on an industrial scale, it is desired to carry out the crystallization treatment by adding the second solvent to the aromatic hydrocarbon used as the reaction solvent in which the bisphenol monoester and impurities are dissolved.

In the present invention, it is preferred to use the first solvent in an amount of about 15-150% by weight based on the amount of the bisphenol monoester of the formula (I). It is preferred to use the second solvent in a mixing ratio of about 0.3-4 times the weight of the first solvent. If amounts of the first solvent and the second solvent are outside the above ranges, reduction in quality or yield of the desired product may be caused or deposition of scale on crystallizing apparatuses may occur. This is not preferred.

The crystallizing operation is generally carried out by first completely dissolving a crude product using the first solvent alone at a boiling temperature or lower and then adding the second solvent to the solution and, if necessary, adding a seed crystal which acts as a nucleus for crystal, and gradually cooling the solution to precipitate crystal. It is also possible in some cases to carry out the crystallization by simultaneously using the first solvent and the second solvent and dissolving the crude product therein. Furthermore, when the aromatic hydrocarbon solvent is used in the reaction step, the second solvent is added to the reaction mixture which is in the form of solution or from which a predetermined amount of the solvent has been removed by distillation or the like to increase concentration of the bisphenol monoester and subsequently, the above-mentioned operation can be effected. The precipitated crystal is separated from the mother liquor by filtration or the like, washed and dried to obtain the desired purified product.

According to the production process of the present invention, the desired product of the formula (I) having a high purity can be efficiently and economically produced, with high yield, continuously from the dialkylphenol without isolating the bisphenol compound. Therefore, this process is useful as a process for producing the bisphenol monoester of the formula (I) on an industrial scale.

Furthermore, according to the purification process of the present invention, the desired product of the formula (I) having a high purity can be efficiently and economically produced with high yield. Therefore, this process is useful as a purification process in production of the bisphenol monoester of the formula (I) on an industrial scale.

The present invention will be explained in more detail with reference to the following Examples, which are only illustrative but not limitative to the scope of the invention. In the Examples, parts and percent (%) are based on the weight unless otherwise indicated.

EXAMPLE 1

In a reactor equipped with a thermometer, a stirrer, a reflux condenser and a dropping device were charged 2344 parts of 2,4-di-t-pentylphenol, 200 parts of xylene, 47 parts of an anionic surface active agent, 95 parts of 78% concentrated sulfuric acid and 771 parts of 30% aqueous acetaldehyde solution, and reaction was allowed to proceed with keeping the temperature at 90°-100° C. for 7 hours with stirring. After completion of the reaction, 3600 parts of xylene was introduced into the reaction mixture. After the aqueous layer was separated and removed, the organic layer was washed with water until it became neutral and then, water was distilled out of the system under a reduced pressure of about 200 mmHg at 90°-110° C. with refluxing the solvent.

After the resulting condensation reaction mixture was cooled, 448 parts of acrylic acid and 1290 parts of triethylamine were charged in the reactor and the air in the reactor was replaced with nitrogen. Then, 634 parts of phosphorus oxychloride was added dropwise and the reactor was kept at 40° C. for 1 hour. Thereafter, the organic layer was washed with water until it became neutral and xylene was distilled off under reduced pressure.

Then, methanol was added to the distillation residue to carry out crystallization thereby to obtain 2226 parts of a white crystalline 2-[1-(2-hydroxy-3,5-di-t-pentylphenyl)ethyl]-4,6-di-t-pentylphenyl acrylate having a melting point of 119°-121° C. (yield: 80.5% based on dialkylphenol)

EXAMPLE 2

Experiment was effected in the same manner as in Example 1 except that toluene was used in place of xylene.

EXAMPLE 3

The procedure of Example 1 was repeated except that 535 parts of methacrylic acid was used in place of acrylic acid, thereby obtaining 2249 parts of white crystalline 2-[1-(2-hydroxy-3,5-di-t-pentylphenyl)ethyl]-4,6-di-t-pentylphenyl methacrylate having a melting point of 103°-105° C.

EXAMPLE 4

The procedure of Example 1 was repeated except that 2063 parts of 2,4-di-t-butylphenol was used in place of 2,4-di-t-pentylphenol and toluene was used in place of xylene as a solvent, thereby obtaining 2088 parts of white crystalline 2,4-di-t-butyl-6-[1-(3,5-di-t-butyl-2-hydroxyphenyl)ethyl]phenyl acrylate having a melting point 190°-192° C.

EXAMPLE 5

In the same reactor as used in Example 1 were charged 1643 parts of 2-t-butyl-4-methylphenol, 800 parts of xylene, 14 parts of an anionic surface active agent, 3 parts of 96% concentrated sulfuric acid and 456 parts of 37% aqueous formaldehyde solution, and reaction was allowed to proceed for 3 hours with keeping the temperature at 90°-95° C. under stirring. After completion of the reaction, 890 parts of xylene was introduced therein, followed by effecting the same after-treatments and refluxing dehydration as in Example 1. The reaction mixture was cooled and then, 354 parts of acrylic acid and 1057 parts of triethylamine were charged therein and the air in the reactor was replaced with nitrogen. Thereafter, 464 parts of phosphorus oxychloride was added dropwise and the reactor was kept at 80° C. for 1 hour.

Then, the same after-treatments and crystallization operation as in Example 1 were carried out to obtain 1564 parts of white crystalline 2-t-butyl-6-(3-t-butyl-2-hydroxy-5-methylbenzyl)-4-methylphenyl acrylate having a melting point of 132°-134° C.

EXAMPLE 6

The procedure of Example 5 was repeated except that toluene was used in place of xylene and 423 parts of methacrylic acid was used in place of acrylic acid, thereby obtaining 1718 parts of white crystalline 2-tbutyl-6-(3-t-butyl-2-hydroxy-5-methylbenzyl)-4-methylphenyl methacrylate having a melting point of 144-146° C.

Results of the reactions in Examples 1-6 are shown in Table 1.

TABLE 1

| | Isolated yield (%) | | | Quality | |
| --- | --- | --- | --- | --- | --- |
| | Bisphenol compound *1 | Bisphenol monoester *2 | *3 | Total *4 | Purity (%) | Melting point (°C.) |
| Example 1 | 94.0 | 85.6 | 64.9 | 80.5 | 99.3 | 119-121 |
| Example 2 | 94.0 | 85.4 | 64.7 | 80.3 | 99.3 | 119-121 |
| Example 3 | 94.0 | 83.7 | 63.5 | 78.7 | 98.5 | 103-105 |
| Example 4 | 93.8 | 90.1 | 68.2 | 84.5 | 99.7 | 190-192 |
| Example 5 | 95.8 | 81.1 | 79.3 | 77.7 | 98.0 | 132-134 |
| Example 6 | 95.8 | 87.6 | 85.6 | 83.9 | 99.8 | 144-146 |

*1: Based on dialklphenol
*2: Based on bisphenol
*3: Based on carboxylic acid
*4: Bisphenol monoester (based on dialkylphenol)

REFERENCE EXAMPLE 1

In a reactor equipped with a thermometer, a stirrer, a reflux condenser and a dropping device were charged 234.4 parts of 2,4-di-t-pentylphenol, 20 parts of xylene, 4.7 parts of an anionic surface active agent, 9.5 parts of 78% concentrated sulfuric acid and 77.1 parts of 30% aqueous acetaldehyde solution, and reaction was allowed to proceed for 7 hours keeping the temperature at 90°-100° C. under stirring. After completion of the reaction, 360 parts of xylene was introduced into the reaction mixture. After the aqueous layer was separated and removed, the organic layer was washed with water until it became neutral and then, water was distilled out of the system under a reduced pressure of about 200 mmHg at 90°-110° C. with refluxing the solvent. After the resulting condensation reaction mixture was cooled, 44.8 parts of acrylic acid and 129.0 parts of triethylamine were charged in the reactor, and the air in the reactor was replaced with nitrogen. Then, 63.4 parts of phosphorus oxychloride was added dropwise and the reactor was kept at 40° C. for 1 hour. Thereafter, the organic layer was washed with water until it became neutral, and the solvent was completely distilled off under reduced pressure to obtain 252.5 parts of a crystalline distillation residue containing 2-[1-(2-hydroxy-3,5-di-t-pentylphenyl)ethyl]-4,6-di-t-pentylphenyl acrylate. This residue was analyzed to find that it contained 87.5% of monoester, 12.2% of by-products and 0.2% of unreacted materials.

REFERENCE EXAMPLE 2

The procedure of Reference Example 1 was repeated except that 53.5 parts of methacrylic acid was used in place of acrylic acid, thereby obtaining 281.4 parts of a crystalline distillation residue containing 2-[1-(2-hydroxy-3,5-di-t-pentylphenyl)ethyl]-4,6-di-t-pentylphenyl methacrylate. This residue was analyzed to find that it contained 87.0% of monoester, 0.2% of unreacted materials and 12.7% of by-products.

REFERENCE EXAMPLE 3

In the same reactor as used in Reference Example 1 were charged 164.3 parts of 2-t-butyl-4-methylphenol, 80 parts of xylene, 1.4 parts of an anionic surface active agent, 0.3 part of 96% concentrated sulfuric acid and 45.6 parts of 37% aqueous formaldehyde solution, and reaction was allowed to proceed for 3 hours with keeping the temperature at 90°-95° C. After completion of the reaction, 89 parts of xylene was introduced thereinto, followed by effecting the same after-treatments and refluxing dehydration as in Reference Example 1. The reaction mixture was cooled and then, 35.0 parts of acrylic acid and 105.7 parts of triethylamine were charged in the reactor and the air in the reactor was replaced with nitrogen. Thereafter, 46.4 parts of phosphorus oxychloride was added dropwise and the reactor was kept at 80° C. for 1 hour.

Then, the same operation as in Reference Example 1 was conducted to obtain 190.8 parts of a crystalline distillation residue containing 2-t-butyl-6-(3-t-butyl-2-hydroxy-5-methylbenzyl)-4-methylphenyl acrylate. It was confirmed that the residue contained 85.5% of monoester, 4.5% of diester, 2.9% of unreacted materials and 7.1% of by-products.

REFERENCE EXAMPLE 4

The procedure of Reference Example 3 was repeated except that 42.3 parts of methacrylic acid was used in place of acrylic acid, thereby obtaining 197.0 parts of a crystalline distillation residue containing 2-t-butyl-6-(3-t-butyl-2-hydroxy-5-methylbenzyl)-4-methylphenyl methacrylate. It was confirmed that this residue contained 92.5% of monoester, 3.3% of unreacted materials and 4.2% of by-products. No diester was detected.

REFERENCE EXAMPLE 5

The procedure of Reference Example 1 was repeated except that 206.3 parts of 2,4-di-t-butylphenol was used in place of 2,4-di-t-pentylphenol and toluene was used in place of xylene as a solvent, thereby obtaining 231.1 parts of a crystalline distillation residue containing 2,4-di-t-butyl-6-[1-(3,5-di-t-butyl-2-hydroxyphenyl)ethyl]phenyl acrylate. It was confirmed that this residue contained 97.0% of monoester, 0.5% of unreacted materials and 2.4% of by-products.

EXAMPLE 7

Fifty parts of the distillation residue obtained in Reference Example 1 was dissolved in 9 parts of xylene at 85° C. and then, 22.5 parts of methanol was gradually added thereto under stirring and 0.1 part of seed crystal was introduced thereinto at 55° C. Thereafter, the mixture was kept for 1 hour at a temperature in the range of 55°–50° C. to precipitate crystal and was gradually cooled to 10° C., and the resulting crystal was filtered off and washed with methanol. Thereafter, the crystal was dried at 60° C. under reduced pressure to obtain 40.5 parts of white crystalline 2-[1-(2-hydroxy-3,5-di-t-pentylphenyl)ethyl]-4,6-di-t-pentylphenyl acrylate having a melting point of 119°–121° C.

EXAMPLES 8 and 9

The procedure of Example 7 was repeated except that isopropanol was used in place of methanol in Example 8 and acetonitrile was used in place of methanol in Example 9. The desired white crystals were obtained.

EXAMPLE 10

The procedure of Example 7 was repeated except that toluene was used in place of xylene, thereby obtaining the desired white crystal.

EXAMPLE 11

The procedure of Example 7 was repeated except that 50 parts of the distillation residue obtained in Reference Example 2 was used and xylene was used in an amount of 8 parts and methanol was used in an amount of 24 parts, thereby obtaining 39.8 parts of white crystalline 2-[1-(2-hydroxy-3,5-di-t-pentylphenyl)ethyl]-4,6-di-tpentylphenyl methacrylate having a melting point of 103°–105° C.

EXAMPLE 12

Fifty parts of the distillation residue obtained in Reference Example 3 was dissolved in 11 parts of xylene at 110° C. and then the solution was cooled to 85° C. under stirring and 0.1 part of seed crystal was introduced thereinto at the same temperature. Crystal was precipitated with gradually cooling the solution and 36 parts of methanol was added at 50° C., followed by cooling to 20° C. The crystal was filtered off at that temperature, washed with methanol and dried at 60° C. under reduced pressure to obtain 41.0 parts of white crystalline 2-t-butyl-6-(3-t-butyl-2-hydroxy-5-methylbenzyl)-4-methylphenyl acrylate having a melting point of 132°–134° C.

EXAMPLES 13 and 14

The procedure of Example 12 was repeated except that n-butanol was used in place of methanol in Example 13 and acetonitrile was used in place of methanol in Example 14, thereby obtaining the desired white crystals.

EXAMPLE 15

The procedure of Example 12 was repeated except that toluene was used in place of xylene, thereby obtaining the desired white crystal.

EXAMPLE 16

The procedure of Example 12 was repeated except that 50 parts of the distillation residue obtained in Reference Example 4 was used, thereby obtaining 43.7 parts of white crystalline 2-t-butyl-6-(3-t-butyl-2-hydroxy-5methylbenzyl)-4-methylphenyl methacrylate having a melting point of 144°–146° C.

EXAMPLE 17

Fifty parts of the distillation residue obtained in Reference Example 5 was dissolved in 65 parts of toluene at 100° C. and then the solution was gradually cooled under stirring to precipitate crystal. Twentyfive parts of methanol was gradually added at 80° C. followed by cooling to 20° C., and the resulting crystal was filtered off at that temperature. The crystal was washed with methanol and dried at 60° C. under reduced pressure to obtain 45.1 parts of white crystalline 2,4-di-t-butyl-6-[1-(3,5-di-t-butyl-2-hydroxyphenyl)ethyl]phenyl acrylate having a melting point of 190°–192° C.

Results of crystallization obtained in the above Examples 7–17 are shown in Table 2.

TABLE 2

| | Crystallizing solvents | Crystallizing yield (%) | Quality | | Melting point (°C.) |
| | | | Purity (%) | Transmittance* (%) | |
| --- | --- | --- | --- | --- | --- |
| Example 7 | xylene/methanol | 91.9 | 99.3 | 98.5 | 119–121 |
| Example 8 | xylene/isopropanol | 91.7 | 99.3 | 98.7 | 119–121 |
| Example 9 | xylene/acetonitrile | 92.0 | 99.3 | 98.0 | 119–121 |
| Example 10 | toluene/methanol | 92.2 | 99.4 | 98.7 | 119–121 |
| Example 11 | xylene/methanol | 90.1 | 98.5 | 98.5 | 103–105 |
| Example 12 | xylene/methanol | 94.0 | 98.0 | 99.6 | 132–134 |
| Example 13 | xylene/n-butanol | 93.5 | 98.2 | 99.8 | 132–134 |
| Example 14 | xylene-acetonitrile | 94.0 | 98.0 | 99.5 | 132–134 |
| Example 15 | toluene/methanol | 93.8 | 98.1 | 99.7 | 132–134 |
| Example 16 | xylene-methanol | 94.1 | 99.8 | 99.3 | 144–146 |
| Example 17 | toluene/methanol | 92.7 | 99.7 | 98.0 | 190–192 |

*Transmitance of a solution prepared by dissolving 2.5 g of sample in tetrahydrofuran to make 20 ml at a wavelength of 425 mm.

What is claimed is:
1. A process for producing a bisphenol monoester represented by the formula (I):

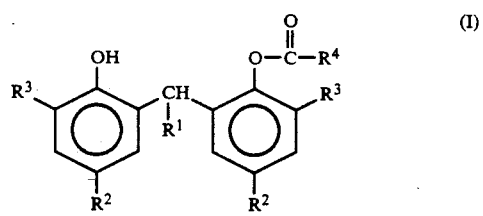

wherein $R^1$ is hydrogen or an alkyl of 1 to 3 carbon atoms, $R^2$ and $R^3$ independently of one another are each an alkyl of 1 to 5 carbon atoms, and $R^4$ is an alkyl of 1 to 3 carbon atoms, an alkenyl of 2 to 4 carbon atoms or phenyl, which process comprises the steps of:

subjecting an aldehyde represented by the formula (II):

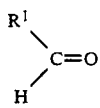     (II)

wherein R¹ is as defined above, to a condensation reaction with a dialkylphenol represented by the formula (III):

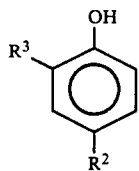     (III)

wherein R² and R³ are as defined above, in a solvent selected from the group consisting of aliphatic hydrocarbons of 6 to 10 carbons atoms and aromatic hydrocarbons of 6 to 12 carbon atoms, to obtain an organic layer containing a bisphenol compound represented by the formula (IV):

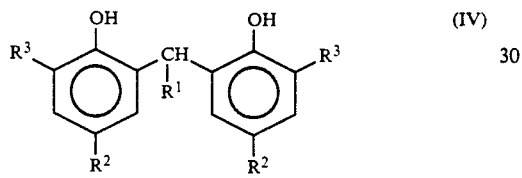     (IV)

wherein R¹, R² and R³ are as defined above; subjecting the organic layer containing the bisphenol compound to a dehydration treatment; and subjecting the dehydrated organic layer, without isolating said bisphenol compound, to a reaction with a carboxylic compound represented by the formula (V):

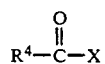     (V)

wherein R⁴ is as defined above, and X is hydroxyl, halogen, an alkoxy of 1 to 3 carbon atoms, or a group of

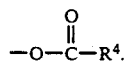

2. The process of claim 1, wherein the solvent is an aliphatic hydrocarbon selected from the group consisting of n-hexane, n-heptane, n-octane, n-nonane, n-decane and cyclohexane, or an aromatic hydrocarbon selected from the group consisting of benzene, toluene, ethylbenzene, xylene, cumene, cymene and chlorobenzene.

3. The process of claim 2, wherein the solvent is an aromatic hydrocarbon selected from the group consisting of toluene and xylene.

4. The process of claim 1, wherein the solvent is used in an amount of 1 to 100% by weight based on the amount of the dialkylphenol of the formula (III) in the reaction between the aldehyde of the formula (II) and the dialkylphenol of the formula (III).

5. The process of claim 1, wherein the reaction mixture obtained by the condensation reaction between the aldehyde of the formula (II) and the dialkylphenol of the formula (III) is mixed with an additional amount of the solvent to separate an organic layer and an aqueous layer, and the organic layer is subjected to the dehydration treatment.

6. The process of claim 5, wherein the additional amount of the solvent is at least 30% by weight based on the amount of the dialkylphenol of the formula (III) used in the condensation reaction.

7. The process of claim 1, wherein the dehydration treatment is effected by heating or by using a dehydrating agent.

8. The process of claim 7, wherein the dehydration treatment is effected by reflux heating.

9. The process of claim 1, wherein the organic layer obtained by the condensation reaction between the aldehyde of the formula (II) and the dialkylphenol of the formula (III) is dehydrated to the water content of at most 0.1% by weight.

10. The process of claim 1, wherein the carboxylic compound of the formula (V) is a carboxylic acid represented by the formula (VI),

     (VI)

wherein R⁴ is as defined in claim 1, and the reaction between the carboxylic acid and the bisphenol compound of the formula (IV) is effected in the presence of a dehydrohalogenating agent and using a halogenating agent.

11. The process of claim 10, where%n the dehydrohalogenating agent is a tertiary amine or a pyridine compound, and the halogenating agent is selected from the group consisting of phosphorus oxychloride, phosphorus oxybromide, o-toluenesulfonyl chloride and p-toluenesulfonyl chloride.

12. The process of claim 10, wherein the dehydrohalogenating agent is triethylamine.

13. The process of claim 10, wherein the halogenating agent is phosphorus oxychloride.

14. The process of claim 1, wherein R⁴ in the formulas (I) and (V) is the alkenyl.

15. The process of claim 14, wherein the bisphenol monoester of the formula (I) is selected from the group consisting of
2-[1-(2-hydroxy-3,5-di-t-pentylphenyl)ethyl]-4,6-di-t-pentylphenyl acrylate,
2-[1-(2-hydroxy-3,5-di-t-pentylphenyl)ethyl]-4,6-di-t-pentylphenyl methacrylate,
2-t-butyl-6-(3-t-butyl-2-hydroxy-5-methylbenzyl)-4-methylphenyl acrylate,
2-t-butyl-6-(3-t-butyl-2-hydroxy-5-methylbenzyl)-4-methylphenyl methacrylate, and 2,4-di-t-butyl-6-[1-(3,5-di-t-butyl-2-hydroxy-phenyl)ethyl]phenyl acrylate.

16. A process for purifying a bisphenol monoester represented by the formula (I),

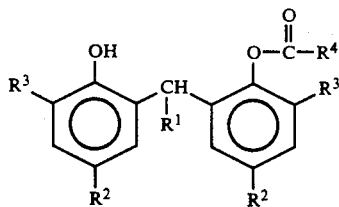

(I)

wherein $R^1$ is hydrogen or an alkyl of 1 to 3 carbon atoms, $R^2$ and $R^3$ independently of one another are each an alkyl of 1 to 5 carbon atoms, and $R^4$ is an alkyl of 1 to 3 carbon atoms, an alkenyl of 2 to 4 carbon atoms or phenyl, which process comprises crystallizing said bisphenol mnoester from a mixed solvent comprising a first solvent which is an aromatic hydrocarbon of 6 to 12 carbon atoms and a second solvent selected from the group consisting of alcohols of 1 to 8 carbon atoms and aliphatic nitriles of 2 to 3 carbon atoms.

17. The process of claim 16, wherein the first solvent is an aromatic hydrocarbon selected from the group consisting of benzene, toluene, xylene, ethylbenzene, cumene, cymene and chlorobenzene, and the second solvent is an alcohol selected from the group consisting of methanol, ethanol, n-propanol, isopropanol, n-butanol, isobutanol, tert-butanol, n-pentanol, n-octanol, 2-ethylhexanol and cyclohexanol, or an aliphatic nitrile selected from the group consisting of acetonitrile an propionitrile.

18. The process of claim 17, wherein the first solvent is toluene or xylene, and the second solvent is methanol.

19. The process of claim 16, wherein the first solvent is used in an amount of 15 to 150% by weight based on the amount of the bisphenol monoester of the formula (I), and the second solvent is used in a ratio of 0.3 to 4 times the weight of the first solvent.

20. The process of claim 16, wherein the crystallizing is effected by preparing a solution of the bisphenol monoester of the formula (I) in the first solvent along, and then adding the second solvent to the solution followed by cooling to precipitate a purified crystal of the bisphenol monoester.

21. The process of claim 20, wherein the solution of the bisphenol monoester in the first solvent alone is a reaction mixture obtained in the production of the bisphenol monoester or a solution in which the first solvent used in the production of the bisphenol monoester is partially removed from the reaction mixture.

22. The process of claim 16, wherein $R^4$ in the formula (I) is the alkenyl.

23. The process of claim 22, wherein the bisphenol monoester of the formula (I) is selected from the group consisting of
2-[1-(2-hydroxy-3,5-di-t-pentylphenyl)ethyl]-4,6-di-t-pentylphenyl acrylate,
2-[2-(2-hydroxy-3,5-di-t-pentylphenyl)ethyl]-4,6-di-t-pentylphenyl methacrylate,
2-t-butyl-6-(3-t-butyl-2-hydroxy-5-methylbenzyl)-4-methylphenyl acrylate,
2-t-butyl-6-(3-t-butyl-2-hydroxy-5-methylbenzyl)-4-methylphenyl methacrylate, and
2,4-di-t-butyl-6-[1-(3,5-di-t-butyl-2-hydroxy-phenyl)ethyl]phenyl acrylate.

* * * * *